April 7, 1936. J. H. NICOLAS Plant Pat. 171
ROSE
Filed Nov. 19, 1935
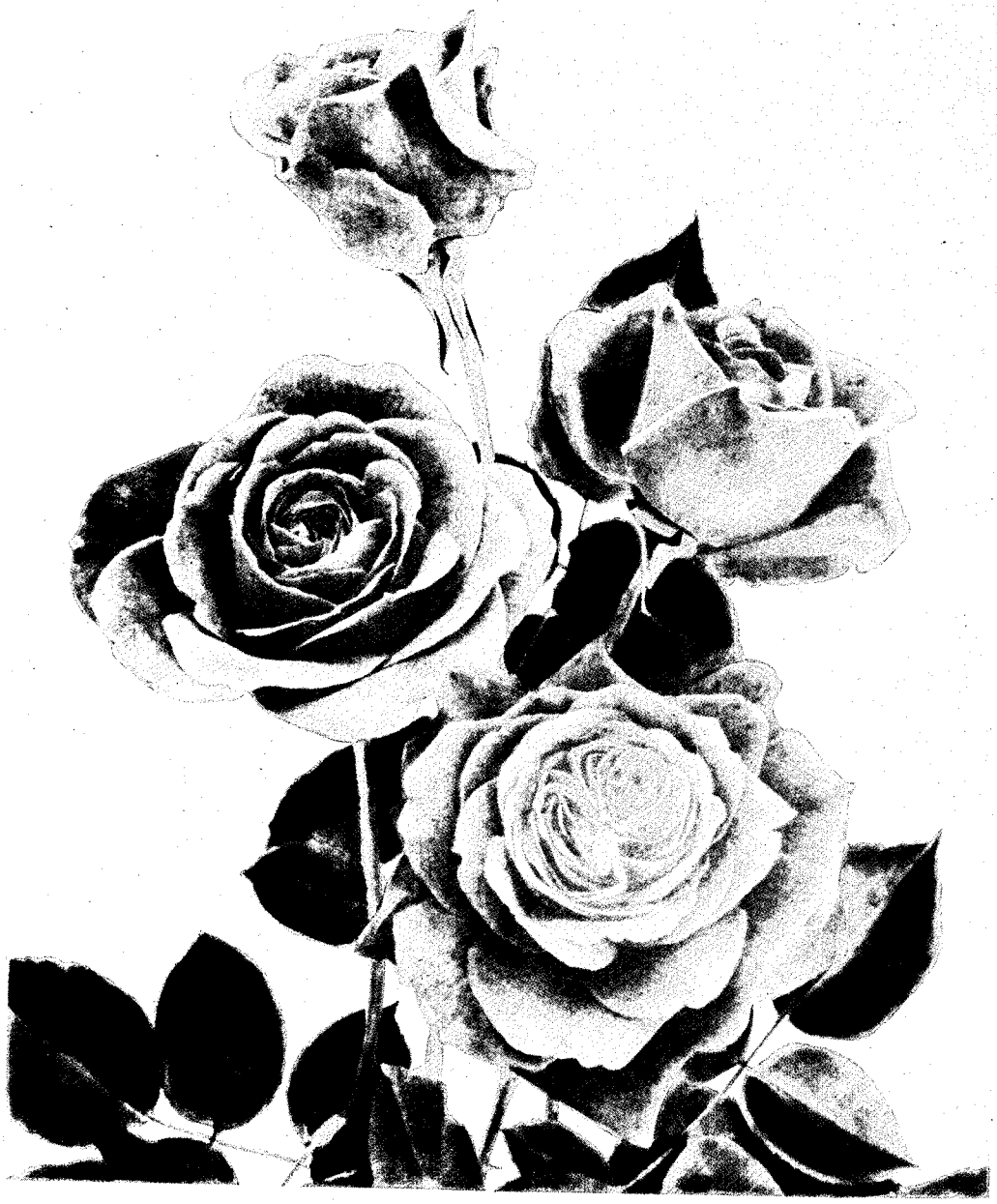
Inventor
J. H. Nicolas
By Robert Robb
attorneys Patented Apr. 7, 1936

UNITED STATES PATENT OFFICE

171

ROSE

Jean H. Nicolas, Newark, N. Y., assignor to
Jackson & Perkins Company, Newark, N. Y.

Application November 19, 1935, Serial No. 50,592

1 Claim. (Cl. 47—61)

The present invention relates to a new and distinct variety of rose plant, the result of a definite effort to produce a new strain of ever-blooming rose more vigorous and more hardy than the usual run of hybrid teas, and of a color more permanent than any other red rose now in commerce either as a cut flower or garden rose.

The foregoing objective has been attained by crossing of the varieties Dame Edith Helen and Scorcher to produce a red rose of the fullness, size and perfume of the former with the color, vigor, constitution and hardiness of the latter.

It should be noted that the variety Scorcher is a new type of climber introduced from Australia and characterized by its distinctive improvement over existing types as evidenced by its unusually large and tough foliage and the unprecedented brilliant flashy red color of its bloom. The desirable characters referred to of each of the prior varieties have been partly reproduced in the hybrid of this invention while the form and fragrance of the Dame Edith Helen have been maintained. It is notable also that the color of the bloom of this new variety is constant and homogeneous or uniform at all stages—scarlet crimson with a deep velvety sheen. Flowering of the plants is continuous, the bloom being perfect at all times regardless of season, and carried on a long upright stem.

The plant is unusually vigorous for a hybrid tea and assumes when well grown the proportions of a medium size hybrid perpetual plant. Tests under glass have proved the new variety to be a good florist rose as well as a good garden rose.

Asexual reproductions have proved the characters of the present rose to be fixed.

The following is a detail description of the new variety, all reference to color therein according with the Gravereaux system:

Parentage:
- Seedling.
- Seed parent—Dame Edith Helen.
- Pollen parent—Scorcher.

Classification:
- Botanic and commercial—Hybrid tea.

*Flower*

Blooming habit:
- Location where observations were made—Jackson & Perkins Company nurseries, test gardens, various florist greenhouses.
- *Blooms.*—Continuous, very profuse.

Bud:
- *Size.*—Very large.
- *Form.*—Urn shape; unaffected by wet or hot weather.
- *Color.*—When sepals first divide—deep crimson. When petals begin to unfurl—scarlet crimson. When half blown: Inside of petals—velvety crimson, reverse of petals—satiny crimson.
- *Sepals.*—Smooth edge; curl back when bud half open.
- *Calyx.*—Shape—funnel. Size—broad. Aspect—smooth. Odor when rubbed—none.
- *Peduncle.*—Length — very long. Aspect — smooth. Color—medium green and bronzy. Strength—erect, slender.
- *Opening.*—Opens well, is not affected by adverse conditions.

Bloom:
- *Size.*—Very large; average size when fully expanded four inches.
- *Borne.*—Singly.
- *Stems.*—Long, normal.
- *Form.*—When first open, flat.
- *Permanence.*—Outer petals curl back.
- *Petalage.*—Very double (many petals and stamens hidden). Number of petals under normal conditions—75.
- *Color.*— Center of flower — crimson scarlet. Outer petals—crimson. Base of petals (aiglet)—crimson scarlet. Inside of petals, reverse of petals, and general tonality from a distance—crimson scarlet.
- *Variegations.*—None.
- *Discoloration.*—General tonality first, second and third days—scarlet crimson.

Petals:
- *Texture.*—Thick, unaffected by wet or hot weather.
- *Appearance.*—Inside—velvety. Outside — satiny.
- *Form.*—Round.
- *Arrangement.*—Imbricated (regularly arranged shinglelike); center slightly quartered. Petaloids in center—none.
- *Persistence.*—Drop off cleanly.
- *Fragrance.*—Strong. Nature—"Old Rose perfume" (Centifolia).
- *Lasting quality.*—On the plant and as cut flowers, very long.

Genital organs:
- *Stamens, anthers.*—Few. Color—yellow. Arrangement—regular around styles.
- *Stamens, filaments (threads).*—Short. Color—reddish.

*Pollen.*—Lemon yellow.
*Styles.*—Bunched, even length, short, heavy.
*Stigmas.*—Color—white.
*Ovaries.*—Some protruding from calyx.

Fruit:
Variety is fertile with its own pollen.
*Form.*—Round.
*Aspect.*—Smooth.
*Color at maturity.*—Scarlet red.
*Sepals.*—Caducous (soon falling).

*Plant*

Form:
Bush.

Growth:
Very vigorous, branching.

Foliage:
Generally five, sometimes seven leaflets.
*Size.*—Large.
*Quantity.*—Abundant.
*Color.*—New foliage: upper side—bronzy, under side—bronzy. Old foliage: upper side—normal green, under side—lighter green.
*Shape.*—Oval pointed.
*Texture.*—Upper side leathery. Under side smooth. Ribs and veins prominent.
*Edge.*—Serrated (saw toothed).
*Serration.*—Single, small.
*Rachis.*—Color, reddish. Under side smooth.
*Stipules.*—Medium, smooth.
*Disease resistance.*—Resistant.

Wood:
*New wood.*—Color—reddish. Bark—smooth.
*Old wood.*—Color—green. Bark—smooth.

Thorns: (Divided into Thorns, Prickles, and Short Needles)
*Thorns.*—Quantity—on main stalks from base, ordinary; on laterals from stalks, few. Form—broad base, medium length straight. Color when young—red. Position—irregular.
*Prickles.*—Quantity—on main stalks, none; on laterals, none.
*Short needles.*—Quantity—on main stalks and laterals, none.

I claim:

A new and distinct variety of rose plant of a new strain characterized by greater vigor and hardiness than the usual run of hybrid teas, and greater permanence of the red color of its bloom than any now in commerce, as shown and described.

JEAN H. NICOLAS.